US009839439B2

United States Patent
Cooper et al.

(10) Patent No.: US 9,839,439 B2
(45) Date of Patent: Dec. 12, 2017

(54) ROTARY INPUT LEVER GIMBAL

(71) Applicant: Intuitive Surgical Operations, Inc., Sunnvale, CA (US)

(72) Inventors: Thomas G. Cooper, Menlo Park, CA (US); S. Christopher Anderson, San Francisco, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 410 days.

(21) Appl. No.: 14/461,322

(22) Filed: Aug. 15, 2014

(65) Prior Publication Data
US 2015/0051619 A1 Feb. 19, 2015

Related U.S. Application Data

(60) Provisional application No. 61/866,235, filed on Aug. 15, 2013.

(51) Int. Cl.
| A61B 19/00 | (2006.01) |
| A61B 17/28 | (2006.01) |
| A61B 34/00 | (2016.01) |
| A61B 34/30 | (2016.01) |
| A61B 17/00 | (2006.01) |

(52) U.S. Cl.
CPC ............. *A61B 17/28* (2013.01); *A61B 34/30* (2016.02); *A61B 34/71* (2016.02); *A61B 2017/00477* (2013.01); *A61B 2034/304* (2016.02); *A61B 2034/306* (2016.02)

(58) Field of Classification Search
CPC ... A61B 17/00234; A61B 17/28; A61B 34/30; A61B 34/70; A61B 34/71; A61B 2034/301
See application file for complete search history.

(56) References Cited

U.S. PATENT DOCUMENTS 6,786,896 B1 * 9/2004 Madhani ............ A61B 19/2203
128/898

OTHER PUBLICATIONS

Vertut, Jean, et al., "Robot Technology; Volume 3A Teleoperation and Robotics Evolution and Development"; 1986 Prentice-Hall, Inc.; Englewood Cliffs, NJ.

* cited by examiner

*Primary Examiner* — Robert N Wieland
(74) *Attorney, Agent, or Firm* — Blakely Sokoloff Taylor & Zafman LLP

(57) ABSTRACT

A force transmission transmits a force received by two rotational inputs to an output gimbal plate. Two capstans receive the rotational input. The capstans drive cables connected to three levers. A cable is connected directly from each of the capstans to one of two levers. Another cable is connected to both capstans and passes over a pulley rotatably coupled to the third lever. Each of three linkages has a first end coupled to one of the three levers and a second end coupled to the output gimbal plate. Rotation of each of the first and the second input capstans causes the three cables to move the three levers such that there is no net movement of the three seconds ends of the linkages with respect to the center of motion of the output gimbal plate. The output gimbal plate may orient a mechanically actuated surgical tool.

27 Claims, 4 Drawing Sheets

ROTARY INPUT LEVER GIMBAL

BACKGROUND

Field

Embodiments of the invention relate to the field of force transmissions; and more specifically, to force transmissions for use in surgical instruments intended for use in minimally invasive surgeries.

Background

Minimally invasive surgery (MIS) (e.g., endoscopy, laparoscopy, thoracoscopy, cystoscopy, and the like) allows a patient to be operated upon through small incisions by using elongated surgical instruments introduced to an internal surgical site. Generally, a cannula is inserted through the incision to provide an access port for the surgical instruments. The surgical site often comprises a body cavity, such as the patient's abdomen. The body cavity may optionally be distended using a clear fluid such as an insufflation gas. In traditional minimally invasive surgery, the surgeon manipulates the tissues by using hand-actuated end effectors of the elongated surgical instruments while viewing the surgical site on a video monitor.

The elongated surgical instruments will generally have an end effector in the form of a surgical tool such as a forceps, a scissors, a clamp, a needle grasper, or the like at one end of an elongate tube. The surgical tool is generally coupled to the elongate tube by one or more articulated sections to control the position and/or orientation of the surgical tool. An actuator that provides the actuating forces to control the articulated section is coupled to the other end of the elongate tube. A means of coupling the actuator forces to the articulated section runs through the elongate tube. The actuator may control an articulated section, such as a "wrist" the orients and manipulates the surgical tool, with means for coupling the actuator forces running through the elongate tube.

It may desirable that the elongate tube be somewhat flexible to allow the surgical instrument to adapt to the geometry of the surgical access path. In some cases, the articulated sections provide access to a surgical site that is not directly in line with the surgical access port. It may be desirable to use cables as the means of coupling the actuator forces to the articulated sections because of the flexibility they provide and because of the ability of a cable to transmit a significant force, a substantial distance, through a small cross-section. However, a cable is generally only able to transmit a force in tension. Thus it is generally necessary to provide two cables to transmit a bidirectional actuating force. The articulated section may be in the form of a gimbal that provides angular motion with two degrees of freedom around a center of rotation. A gimbal can be controlled by three cables.

In view of the above, it is desirable to provide an improved apparatus and method for transmitting actuating forces through an elongate tube of a surgical instrument intended for use in minimally invasive surgeries that uses three cables connected to a gimbal type articulated section.

SUMMARY

A force transmission transmits a force received by two rotational inputs to an output gimbal plate. Two capstans receive the rotational input. The capstans drive cables connected to three levers. A cable is connected directly from each of the capstans to one of two levers. Another cable is connected to both capstans and passes over a pulley rotatably coupled to the third lever. Each of the three levers is coupled to the output gimbal plate by a linkage, such as a cable. Rotation of each of the first and the second input capstans causes the three cables to move the three levers such that there is no net movement of the three second ends of the linkages with respect to the center of motion of the output gimbal plate. The output gimbal plate may orient a mechanically actuated surgical tool.

Other features and advantages of the present invention will be apparent from the accompanying drawings and from the detailed description that follows below.

BRIEF DESCRIPTION OF THE DRAWINGS

The invention may best be understood by referring to the following description and accompanying drawings that are used to illustrate embodiments of the invention by way of example and not limitation. In the drawings, in which like reference numerals indicate similar elements.

DETAILED DESCRIPTION

In the following description, numerous specific details are set forth. However, it is understood that embodiments of the invention may be practiced without these specific details. In other instances, well-known circuits, structures and techniques have not been shown in detail in order not to obscure the understanding of this description.

In the following description, reference is made to the accompanying drawings, which illustrate several embodiments of the present invention. It is understood that other embodiments may be utilized, and mechanical compositional, structural, electrical, and operational changes may be made without departing from the spirit and scope of the present disclosure. The following detailed description is not to be taken in a limiting sense, and the scope of the embodiments of the present invention is defined only by the claims of the issued patent.

The terminology used herein is for the purpose of describing particular embodiments only and is not intended to be limiting of the invention. Spatially relative terms, such as "beneath", "below", "lower", "above", "upper", and the like may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (e.g., rotated 90 degrees or at other orientations) and the spatially relative descriptors used herein interpreted accordingly.

As used herein, the singular forms "a", "an", and "the" are intended to include the plural forms as well, unless the context indicates otherwise. It will be further understood that the terms "comprises" and/or "comprising" specify the presence of stated features, steps, operations, elements, and/or components, but do not preclude the presence or addition of one or more other features, steps, operations, elements, components, and/or groups thereof.

Figure 1:
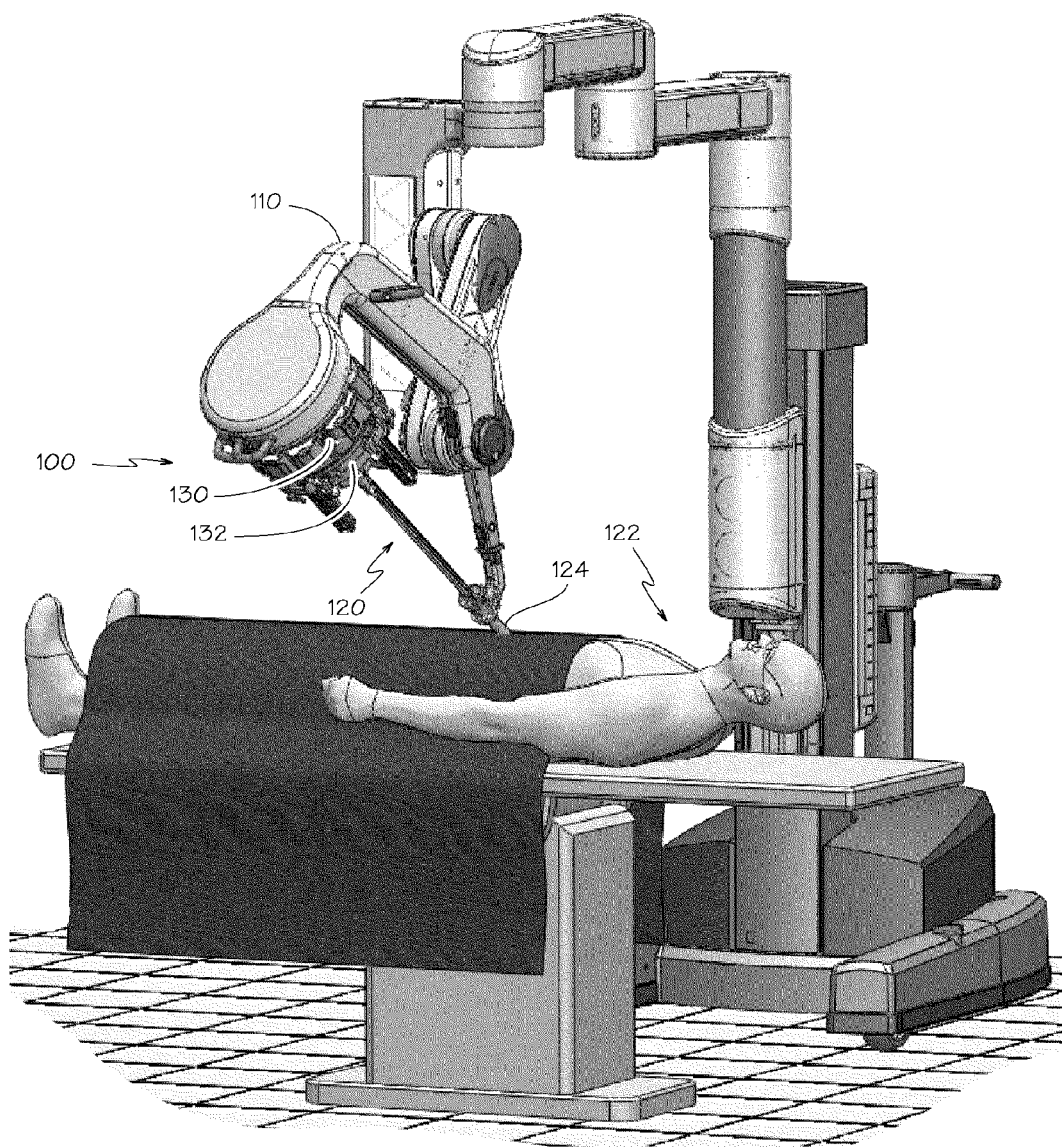
FIG. 1 is a simplified perspective view of a teleoperated surgical system with a mechanically actuated surgical instrument inserted through a port in a patient's abdomen.

FIG. 1 is a simplified diagrammatic perspective view of a teleoperated surgical system 100. The system 100 includes a support assembly 110 mounted to or near an operating table supporting a patient's body 122. The support assembly 110 supports one or more surgical instruments 120 that operate on a surgical site within the patient's body 122.

The term "instrument" is used herein to describe a device configured to be inserted into a patient's body and used to carry out surgical procedures. The instrument includes a surgical tool, such as a forceps, a needle driver, a shears, a monopolar cauterizer, a bipolar cauterizer, a tissue stabilizer or retractor, a clip applier, an anastomosis device, an imaging device (e.g., an endoscope or ultrasound probe), and the like. Some instruments used with embodiments of the invention further provide an articulated support for the surgical tool so that the position and orientation of the surgical tool can be manipulated.

The simplified perspective view of the system 100 shows only a single instrument 120 to allow aspects of the invention to be more clearly seen. A functional teleoperated surgical system would further include a vision system that enables the operator to view the surgical site from outside the patient's body 122. The vision system can include a video monitor for displaying images received by an optical device provided at a distal end of one of the surgical instruments 120. The optical device can include a lens coupled to an optical fiber which carries the detected images to an imaging sensor (e.g., a CCD or CMOS sensor) outside of the patient's body 122. Alternatively, the imaging sensor may be provided at the distal end of the surgical instrument 120, and the signals produced by the sensor are transmitted along a lead or wirelessly for display on the monitor. An illustrative monitor is the stereoscopic display on the surgeon's cart in the da Vinci® Surgical System, marketed by Intuitive Surgical, Inc., of Sunnyvale Calif.

A functional teleoperated surgical system would further include a control system for controlling the insertion and articulation of the surgical instruments 120. This control may be effectuated in a variety of ways, depending on the degree of control desired, the size of the surgical assembly, and other factors. In some embodiments, the control system includes one or more manually operated input devices, such as a joystick, exoskeletal glove, or the like. These input devices control motors, such as servo motors, which, in turn, control the articulation of the surgical assembly. The forces generated by the motors are transferred via drivetrain mechanisms, which transmit the forces from the motors generated outside the patient's body 122 through an intermediate portion of the elongate surgical instrument 120 to a portion of the surgical instrument inside the patient's body 122 distal from the motor. Persons familiar with telemanipulative, teleoperative, and telepresence surgery will know of systems such as the da Vinci® Surgical System and the Zeus® system originally manufactured by Computer Motion, Inc. and various illustrative components of such systems.

The surgical instrument 120 is shown inserted through an entry guide 124, e.g., a cannula in the patient's abdomen. A functional teleoperated surgical system may provide an entry guide manipulator (not shown; in one illustrative aspect the entry guide manipulator is part of the support system 110) and an instrument manipulator (discussed below). The entry guide 124 is mounted onto the entry guide manipulator, which includes a mechanically actuated positioning system for positioning the distal end of the entry guide 124 at the desired target surgical site. The mechanically actuated positioning system may be provided in a variety of forms, such as a serial link arm having multiple degrees of freedom (e.g., six degrees of freedom) or a jointed arm that provides a remote center of motion (due to either hardware or software constraints) and which is positioned by one or more unpowered, lockable setup joints mounted onto a base. Alternatively, the entry guide manipulator may be manually maneuvered so as to position the entry guide 124 in the desired location. In some telesurgical embodiments, the input devices that control the manipulator(s) may be provided at a location remote from the patient (outside the room in which the patient is placed). The input signals from the input devices are then transmitted to the control system, which, in turn, manipulates the manipulators 130 in response to those signals. The instrument manipulator may be coupled to the entry guide manipulator such that the instrument manipulator 130 moves in conjunction with the entry guide 124.

The surgical instrument 120 is detachably connected to the mechanically actuated instrument manipulator 130. The mechanically actuated manipulator includes a coupler 132 to transfer controller motion from the mechanically actuated manipulator to the surgical instrument 120. The instrument manipulator 130 may provide a number of controller motions which the surgical instrument 120 may translate into a variety of movements of the end effector on the surgical instrument such that the input provided by a surgeon through the control system is translated into a corresponding action by the surgical instrument.

Figure 2:
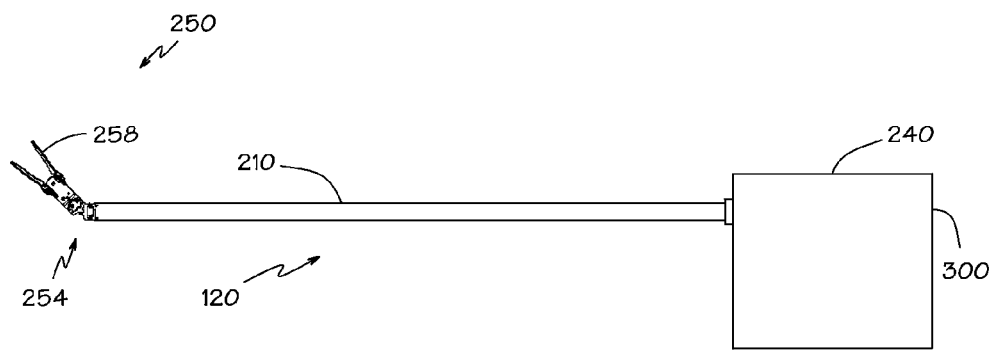
FIG. 2 is a plan view of a surgical instrument for use with a mechanically actuated manipulator.

FIG. 2 is a plan view of an illustrative embodiment of the surgical instrument 120, comprising a distal portion 250 and a proximal control mechanism 240 coupled by an elongate tube 210. The distal portion 250 of the surgical instrument 120 may provide any of a variety of surgical devices such as the forceps 258 shown, a needle driver, a cautery device, a cutting tool, an imaging device (e.g., an endoscope or ultrasound probe), or a combined device that includes a combination of two or more various tools and imaging devices. In the embodiment shown, the surgical tool 258 is coupled to the elongate tube 210 by an articulated section in the form of a "wrist" 254 that allows the orientation of the surgical tool to be manipulated.

Surgical instruments that are used with the invention are controlled by a plurality of flexible cables. Cables provide a means of transmitting forces to the joints that is compact and flexible. A typical elongate tube 210 for a surgical instrument 120 is small, perhaps six millimeters in diameter, roughly the diameter of a large soda straw. The diminutive scale of the mechanisms in the surgical instrument 120 creates unique mechanical conditions and issues with the construction of these mechanisms that are unlike those found in similar mechanisms constructed at a larger scale because forces and strengths of materials do not scale at the same rate as the size of the mechanisms. The cables must fit within the elongate tube 210 and be able to bend as they pass through the joints of the "wrist" 254.

Figure 3:
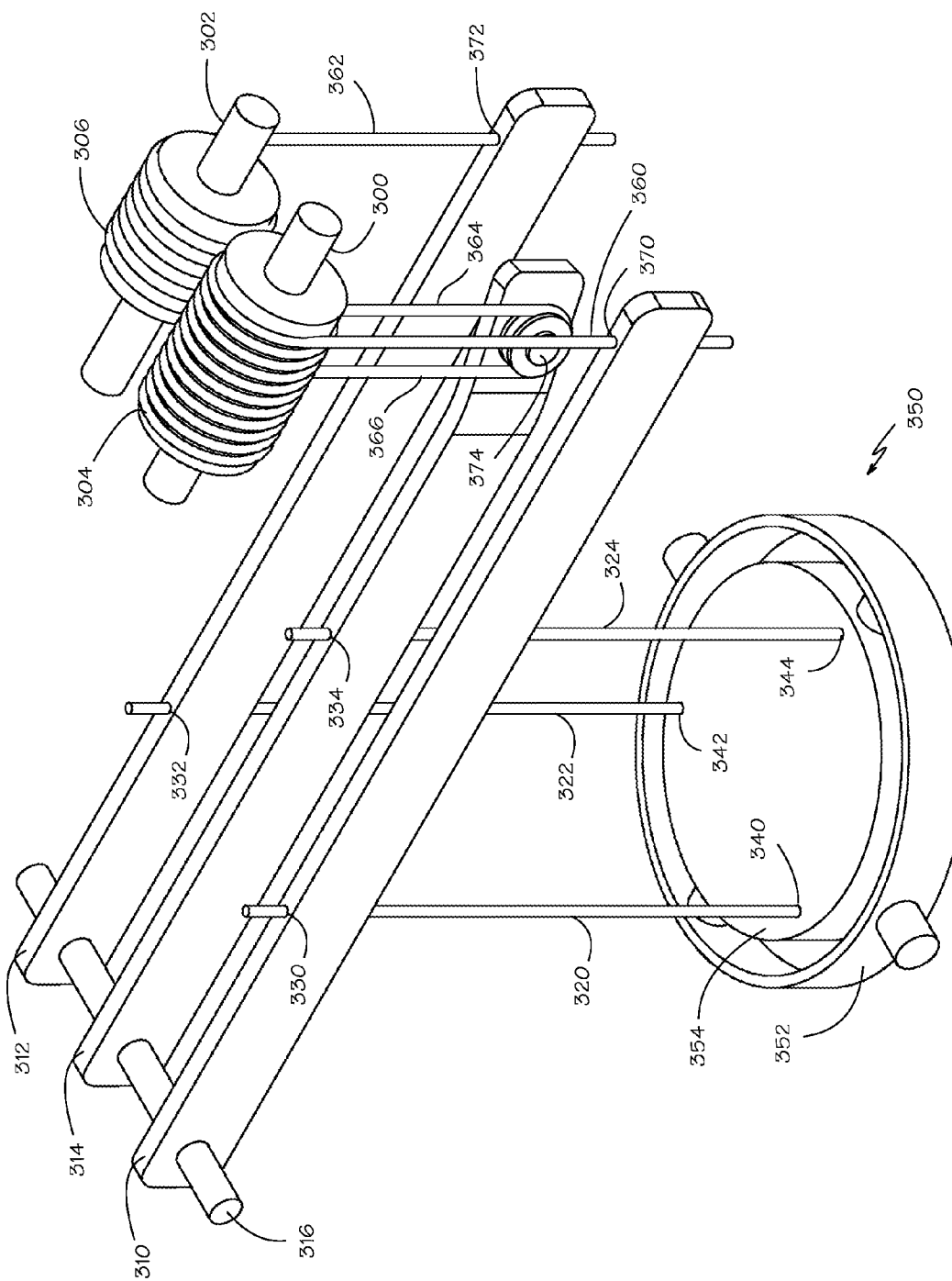
FIG. 3 is a perspective view of a force transmission.

FIG. 3 is a perspective view showing a force transmission mechanism that uses two rotary inputs 300, 302 to control the movement of a gimbal assembly 350. The gimbal assembly includes an outer gimbal 352 that is pivotally supported by a housing (not shown) of the force transmission mechanism and an inner gimbal that acts as an output gimbal plate 354 that is pivotally supported by the outer gimbal. The axes of the inner and outer gimbals intersect and allow the output gimbal plate 354 to move with two degrees of rotational freedom, one for each of the two axes of the gimbal assembly 350. The output gimbal plate 354 has a center of rotation at the intersection of the inner and outer axes.

The force transmission mechanism uses three levers 310, 312, 314 to couple rotation of the two rotary inputs 300, 302 to three linkages 320, 322, 324 that control the movement of the output gimbal plate 354. Each linkage has a first end 330, 332, 334 coupled to one of the three lever 310, 312, 314 and a second end 340, 342, 344 coupled to the output gimbal plate 354. The three linkages may be cables 320, 322, 324 that may be coupled to the gimbal assembly 350 equidistant from a center of motion of the output gimbal plate and uniformly spaced apart.

Since there is no displacement in the center of a gimbal when it rotates on either of the two intersecting axes of rotation, there is no net displacement of the second ends 340, 342, 344 of the three linkages 320, 322, 324 when they are coupled to the output gimbal plate 354 equidistant from a center of motion of the output gimbal plate and uniformly spaced apart as shown. If one of the three linkages is held stationary, then the other two linkages will move with equal and opposite motions. Of course, all three linkages can move simultaneously and their net motions will sum to zero.

The two rotary inputs 300, 302 rotate two input capstans 304, 306. A first cable 360 has a first end coupled to the first input capstan 304 and a second end 370 coupled to the first lever 310. A second cable 362 has a first end coupled to the second input capstan 306 and a second end 372 coupled to the second lever 312. A third cable has a first end 364 coupled to the first input capstan 304 and a second end 366 coupled to the second input capstan 306. The third cable is arranged so that it moves with an opposite motion to the other cable coupled to the same input capstan. Thus when the first input capstan 304 winds onto the first cable 360, the third cable 364 is wound out. In the embodiment shown, the third cable winds in and out equally and opposite to the first and second cables. It will be appreciated that the first, second, and third cables may be portions of a single cable.

The third cable is coupled to the third lever 314 by passing over a pulley 374 that is rotatably coupled to the third lever. This causes rotation of either or both of the two capstans 304, 306 to move the third lever 314. It will be appreciated that a given movement of the third cable will result in one-half that movement of the third lever 314 at the point where the pulley 374 is coupled to the lever.

The force transmission shown in FIG. 3 uses second class levers with the load 330, 332, 334 being coupled to the levers between the pivot 316 and the force 370, 372, 374. It will be appreciated that third class levers could also be used in which case the positions of the loads and the forces would be exchanged. The motion of the load is the motion of the force multiplied by the distance from the pivot to the load divided by the distance from the pivot to the force, a factor that will be less than one for a second class lever. In the force transmission shown in FIG. 3, the multiplying factor is the same for the first 310 and second 312 levers and doubled for the third lever 314. Thus the levers cancel the effect of the pulley on the third cable. As a result, rotation of each of the first and the second input capstans causes the first, second, and third cables to move the first, second, and third levers such that there is no net movement of the three seconds ends of the linkages with respect to the center of motion of the output gimbal plate.

Figures 4, 5:
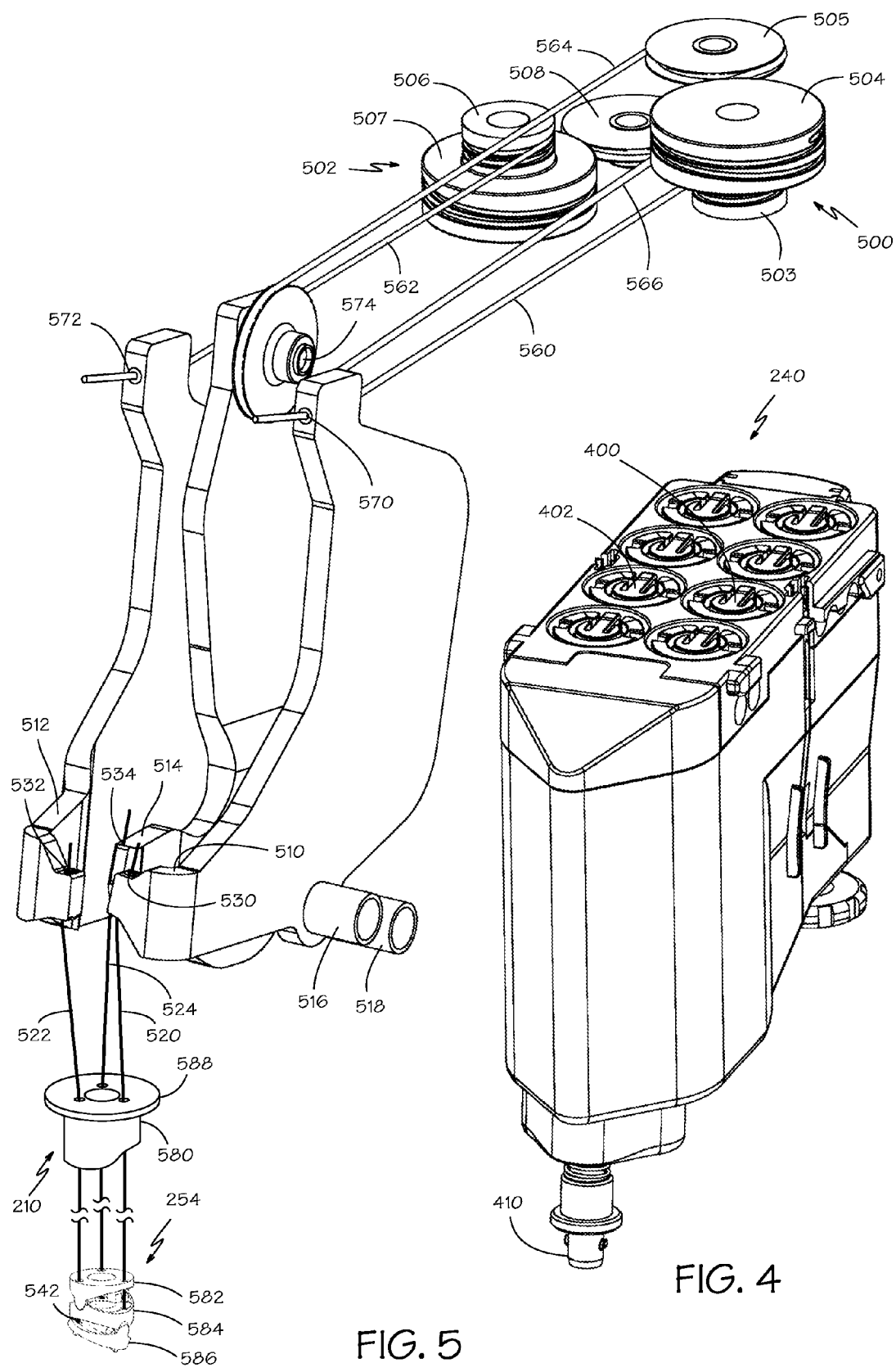
FIG. 4 is a perspective view of a proximal control mechanism of the surgical instrument shown in FIG. 2.
FIG. 5 is a perspective view of another force transmission mechanism.

FIG. 4 is a perspective view of the proximal control mechanism 240 of the surgical instrument 120 shown in FIG. 2. The proximal control mechanism 240 provides at least two rotational inputs 400, 402. The rotational inputs are coupled to actuators, such as servo motors, in the mechanically actuated instrument manipulator 130 to transfer controller motion from the mechanically actuated manipulator to the surgical instrument 120. The proximal end of the elongate shaft 210 opposite the distal end having the surgical tool 258 is also coupled to the proximal control mechanism 240 but is not shown in this figure. The proximal end of the elongate tube 210 would be held in place by the output coupler 410 for the proximal control mechanism 240 shown.

FIG. 5 shows a perspective view of a force transmission mechanism that transfers the forces applied to the two rotational inputs 400, 402 to the articulated section 254 at the distal end of the elongate tube 210. A first end 580 of the elongate tube 210 is adjacent three levers 510, 512, 514, which are part of the proximal control mechanism 240. The output linkages 520, 522, 524 are substantially contained within the tube 210 with the linkages extending from the opposing ends of the tube to connect to the levers and the articulated section 254. A guide plate 588 may be provided to control the location where the output linkages 520, 522, 524 enter the first end 580 of the elongate tube 210 and ensure that the net pay-out and pay-in of the three linkages is zero. The guide plate 588 may also help to keep the linkages from crossing over one another.

Any force applied to move the three levers 510, 512, 514 will be transmitted to move an output gimbal plate 586 in the articulated section 254. It will be appreciated that while the output plate 586 is described as a gimbal plate because it has two degrees of angular freedom, the embodiment shown is not a true gimbal because the axes of rotation for the plate do not intersect and do not lie in the same plane as the plate. The small scale of the joint makes it difficult to construct the joint as a true gimbal. Nonetheless, the output plate 586 does have substantially the same kinematic characteristics as a gimbal and it is therefore helpful to consider the output plate as an output gimbal plate.

The connections to the output gimbal plate 586 are arranged so that for each axis of rotation, there are connections on both sides of the axis that are spaced substantially away from the axis. Thus any movement of the three levers 510, 512, 514 will create tension in at least one of the three output linkages 520, 522, 524. That tension will cause the output gimbal plate 586 to move and apply tension to any of the three output linkages 520, 522, 524 that are not in tension from movement of the three levers 510, 512, 514. Flexible cables can be used for the output linkages because the operation of the force transmission maintains tension in all the output linkages.

It will be appreciated that the proximal control mechanism 240 is substantially larger than the output gimbal plate 586 in the embodiment shown. Therefore it is desirable to use a force transmission that scales the motions of the input gimbal to provide motions that are appropriate for controlling the output gimbal. The mechanisms that provide the controlling motions are generally bulky while the output gimbal is compact. Therefore it is desirable to use a force transmission apparatus that spatially translates the input motions to allow the output gimbal to be compact.

Because of the size of the proximal control mechanism 240, the cables that couple the input capstans to the levers are rather compliant. This compliance is undesirable when controlling a surgical instrument. Providing levers which scale down the motion between the lever input and the lever output reduces the effect of the cable compliance by the square of the lever ratio. For example, using a 2:1 lever ratio reduces the effect of cable compliance by a factor of four.

The force transmission shown in FIG. 5 is conceptually the same as the force transmission shown in FIG. 3. The major differences are that the force transmission shown in FIG. 5 uses first class bell crank levers that allow the force and the load to be at a substantial angle to one another and the levers all provide the same ratio of movement between the input and output with the motion dividing effect of the pulley on the third cable being cancelled by the capstan structure rather than the levers.

The two rotary inputs 400, 402 of the proximal control mechanism 240 are coupled to capstans 500, 502 to control the movement of a gimbal assembly 254. The gimbal assembly includes top gimbal plate 582 that is supported by the elongate tube 210, an intermediate plate 584 that provides rotational pivots, and a bottom gimbal plate that acts as an output gimbal plate 586. The output gimbal plate 586 moves with two degrees of rotational freedom.

The force transmission mechanism uses three levers 510, 512, 514 to couple rotation of the two rotary inputs 400, 402 to three linkages 520, 522, 524 that control the movement of the output gimbal plate 586. Each linkage has a first end 530, 532, 534 coupled to one of the three lever 510, 512, 514 and a second end 540 coupled to the output gimbal plate 586. The three linkages may be cables 520, 522, 524 that may be coupled to the gimbal assembly 254 equidistant from a center of motion of the output gimbal plate and uniformly spaced apart.

Since there is no displacement of the center of rotation of a gimbal, there is no net displacement of the second ends 540, 542, 544 of the three linkages 520, 522, 524 when they are coupled to the output gimbal plate 586 equidistant from a center of motion of the output gimbal plate and uniformly spaced apart as shown. If one of the three linkages is held stationary, then the other two linkages will move with equal and opposite motions. Of course, all three linkages can move simultaneously and their net motions will sum to zero.

Figure 6:
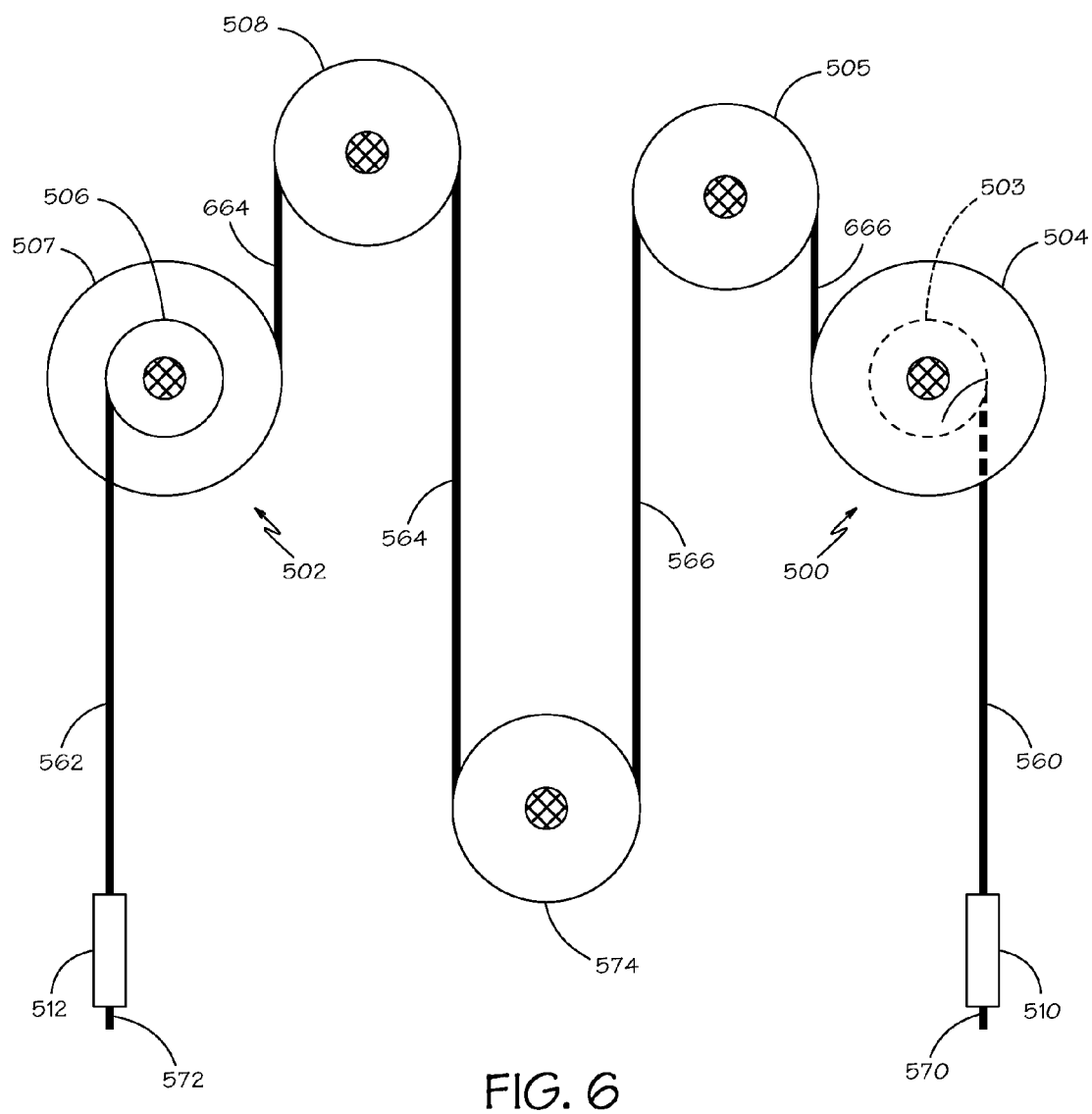
FIG. 6 is a schematic representation of the input capstans and associated cables that are coupled to the levers.

FIG. 6 is a schematic representation of the input capstans 500, 502 and associated cables that are coupled to the levers. The two rotary inputs 400, 402 (FIG. 4) rotate the two input capstans 500, 502. A first cable 560 has a first end coupled to a first portion 503 of the first input capstan 500 and a second end 570 coupled to the first lever 510. A second cable 562 has a first end coupled to a first portion 506 of the second input capstan 502 and a second end 572 coupled to the second lever 512.

A third cable has a first end coupled to a second portion 504 of the first input capstan 500 and a second end coupled to a second portion 507 of the second input capstan 502. The third cable is arranged so that it passes over idler pulleys 505, 508 and moves with an opposite motion to the first and second cables. More particularly, the third cable has a first segment 666 that extends from the second portion 504 of the first input capstan 500 to the first idler pulley 505 and a fourth segment 664 that extends from the second portion 507 of the second input capstan 502 to the second idler pulley 508. Thus when the first input capstan 500 winds in the first cable 560, the third cable is wound out from the first input capstan. Similarly, when the second input capstan 502 winds in the second cable 562, the third cable is wound out from the second input capstan.

The third cable is coupled to the third lever 514 by passing over a pulley 574 that is rotatably coupled to the third lever. More particularly, the third cable has a second segment 566 that extends from the first idler pulley 505 to the third lever pulley 574 and a third segment 564 that extends from the second idler pulley 508 to the third lever pulley. This causes rotation of either or both of the two input capstans 500, 502 to move the third lever 514. It will be appreciated that a given movement of the third cable will result in one-half that movement of the third lever 514 at the point where the pulley 574 is coupled to the lever. The second portions 504, 507 of the input capstans 500, 502 are twice the diameter of the first portions 503, 506. Thus the two portions of each input capstan 500, 502 are in a 2:1 ratio to compensate for the 1:2 ratio of third lever 514 movement resulting from the third cable passing over the third lever pulley 574. As a result, rotation of each of the first and the second input capstans 500, 502 causes the first, second, and third cables to move the first, second, and third levers such that there is no net movement of the three second ends of the linkages with respect to the center of motion of the output gimbal plate.

It will be appreciated that the idler pulleys 505, 508 are to route the cables as required for the arrangement illustrated. Other embodiments of the invention may use different numbers of idler pulleys, idler pulleys in different arrangements, idler pulleys on different cables, or no idler pulleys.

The force transmission shown in FIG. 5 uses first class levers with the load 530, 532, 534 and the force 570, 572, 574 being coupled to the levers on opposite sides of the pivot 516, 518. The use of bell crank levers allows the rotary inputs 400, 402 to be at an angle with respect to the three linkages 520, 522, 524. In the embodiment illustrated, the rotary inputs are approximately perpendicular to the three linkages. This may be advantageous in terms of moving the bulky actuator mechanisms away from the surgical field.

While certain exemplary embodiments have been described and shown in the accompanying drawings, it is to be understood that such embodiments are merely illustrative of and not restrictive on the broad invention, and that this invention is not limited to the specific constructions and arrangements shown and described, since various other modifications may occur to those of ordinary skill in the art. The description is thus to be regarded as illustrative instead of limiting.

What is claimed is:

1. A force transmission comprising:
   a first input capstan and a second input capstan;
   a first lever, a second lever, and a third lever;
   a pulley coupled to the third lever;
   an output gimbal plate having two degrees of rotational freedom about a center of motion of the output gimbal plate;
   three linkages, each linkage having a first end and a second end, the first end of each linkage being coupled to a corresponding unique one of the three levers, and the second end of each linkage being coupled to the output gimbal plate;
   a first cable having a first end coupled to the first input capstan and a second end coupled to the first lever;
   a second cable having a first end coupled to the second input capstan and a second end coupled to the second lever; and a third cable coupled to the first input capstan such that the third cable is wound out by the first input capstan as the first cable is wound in by the first input capstan, coupled to the second input capstan such that the third cable is wound out by the second input capstan as the second cable is wound in by the second input capstan, and coupled to the third lever by passing over the pulley coupled to the third lever.

2. The force transmission of claim 1 wherein the three second ends of the linkages are equidistant from the center of motion of the output gimbal plate and uniformly spaced apart.

3. The force transmission of claim 1 wherein the first lever, the second lever, and the third lever are second class levers.

4. The force transmission of claim 1 wherein the first lever, the second lever, and the third lever are third class levers.

5. The force transmission of claim 1 wherein the first lever, the second lever, and the third lever are first class bell crank levers.

6. The force transmission of claim 5 wherein the bell crank levers each have two arms that are perpendicular to one another.

7. The force transmission of claim 1 wherein the first input capstan and the second input capstan each include a first portion and a second portion, the first portions having a first diameter, the second portions having a second diameter twice the first diameter, the first cable being coupled to the first portion of the first input capstan, the second cable being coupled to the first portion of the second input capstan, and the third cable being coupled to the second portion of the first input capstan and the second portion of the second input capstan.

8. The force transmission of claim 1 wherein the three linkages each comprise flexible cables.

9. The force transmission of claim 8 further comprising a tube having a first end adjacent the first lever, the second lever, and the third lever, and an opposing second end adjacent the output gimbal plate, wherein the three linkages are substantially contained within the tube.

10. A method of operating a mechanically actuated surgical instrument, the method comprising:
receiving a force input with a first input capstan and a second input capstan;
moving a first lever and a second lever with a first cable and a second cable, each of the two cables coupled to a corresponding unique one of the two input capstans;
moving a third lever with a third cable coupled to both of the two input capstans and passing over a pulley coupled to the third lever; and
wherein the three levers are coupled to an articulated joint that supports a surgical end effector with three linkages, each linkage having a first end coupled to one of the three levers and a second end coupled to the articulated joint, rotation of the first and the second input capstans causing the first cable, the second cable, and the third cable to move the first lever, the second lever, and the third lever such that there is no net movement of the three second ends of the linkages with respect to a center of motion of the articulated joint.

11. The method of claim 10 wherein the three second ends of the linkages are equidistant from the center of motion of the articulated joint and uniformly spaced apart.

12. The method of claim 10 wherein the first lever, the second lever, and the third lever are second class levers.

13. The method of claim 10 wherein the first lever, the second lever, and the third lever are third class levers.

14. The method of claim 10 wherein the first lever, the second lever, and the third lever are first class bell crank levers.

15. The method of claim 14 wherein the bell crank levers each have two arms that are perpendicular to one another.

16. The method of claim 10 wherein the first input capstan and the second input capstan each include a first portion having a first diameter to which the first cable and the second cable are coupled and a second portion having a second diameter that is twice the first diameter to which two ends of the third cable are coupled.

17. The method of claim 10 wherein the three linkages comprise flexible cables.

18. The method of claim 17 further comprising passing the three linkages through a tube having a first end adjacent the first lever, the second lever, and the third lever and an opposing second end adjacent the articulated joint wherein the three linkages are substantially contained within the tube.

19. A mechanically actuated surgical instrument comprising:
a first input capstan and a second input capstan that each independently receive a rotational input;
a first lever, a second lever, and a third lever, each lever supported by a pivot;
a pulley coupled to the third lever;
a tube having a first end and an opposing second end;
an output gimbal plate coupled to the second end of the tube and having two degrees of rotational freedom about a center of motion of the output gimbal plate;
a surgical tool coupled to the output gimbal plate;
three linkages, each linkage having a first end and a second end, the first end of each linkage being coupled to a corresponding unique one of the three levers, the second end of each linkage being coupled to the output gimbal plate, and passing between the first end and the second end of the tube such that each linkage is substantially contained within the tube;
a first cable having a first end coupled to the first input capstan and a second end coupled to the first lever;
a second cable having a first end coupled to the second input capstan and a second end coupled to the second lever; and
a third cable coupled to the first input capstan such that the third cable is wound out by the first input capstan as the first cable is wound in by the first input capstan, coupled to the second input capstan such that the third cable is wound out by the second input capstan as the second cable is wound in by the second input capstan, and coupled to the third lever by passing over the pulley coupled to the third lever;
wherein rotation of the first and the second input capstans causes the first cable, the second cable, and the third cable to move the first lever, the second lever, and the third lever such that there is no net movement of the three second ends of the linkages with respect to the center of motion of the output gimbal plate, motion of the output gimbal plate moving the surgical tool.

20. The mechanically actuated surgical instrument of claim 19 wherein the three second ends of the linkages are equidistant from the center of motion of the output gimbal plate and uniformly spaced apart.

21. The mechanically actuated surgical instrument of claim 19 wherein the first lever, the second lever, and the third lever are second class levers.

22. The mechanically actuated surgical instrument of claim 19 wherein the first lever, the second lever, and the third lever are third class levers.

23. The mechanically actuated surgical instrument of claim 19 wherein the first lever, the second lever, and the third lever are first class bell crank levers.

24. The mechanically actuated surgical instrument of claim 23 wherein the bell crank levers each have two arms that are perpendicular to one another.

25. The mechanically actuated surgical instrument of claim 19 wherein the first input capstan and the second input capstan each include a first portion having a first diameter to which the first cable and the second cable are coupled and a second portion having a second diameter that is twice the first diameter to which two ends of the third cable are coupled.

26. The mechanically actuated surgical instrument of claim 19 wherein the three linkages each comprise flexible cables.

27. The force transmission of claim 1 wherein rotation of the first and the second input capstans causes the first cable, the second cable, and the third cable to move the first lever, the second lever, and the third lever such that there is no net movement of the three second ends of the linkages with respect to the center of motion of the output gimbal plate.

* * * * *